US009814267B2

(12) United States Patent
Liu

(10) Patent No.: US 9,814,267 B2
(45) Date of Patent: Nov. 14, 2017

(54) ELECTRONIC CIGARETTE AND ELECTRONIC CIGARETTE DEVICE THEREOF

(71) Applicant: KIMREE HI-TECH INC., Tortola (VG)

(72) Inventor: Qiuming Liu, Huizhou (CN)

(73) Assignee: SHENZHEN KIMSEN TECHNOLOGY CO., LTD., Shenzhen, Guangdong Province (CN)

( * ) Notice: Subject to any disclaimer, the term of this patent is extended or adjusted under 35 U.S.C. 154(b) by 387 days.

(21) Appl. No.: 14/412,415

(22) PCT Filed: Sep. 28, 2012

(86) PCT No.: PCT/CN2012/082290
§ 371 (c)(1),
(2) Date: Dec. 31, 2014

(87) PCT Pub. No.: WO2014/047869
PCT Pub. Date: Apr. 3, 2014

(65) Prior Publication Data
US 2015/0157054 A1 Jun. 11, 2015

(51) Int. Cl.

| | |
|---|---|
| ***A24F 47/00*** | (2006.01) |
| ***A61M 15/06*** | (2006.01) |
| ***A24F 15/12*** | (2006.01) |
| ***H05B 1/02*** | (2006.01) |
| ***H05B 3/40*** | (2006.01) |

(52) U.S. Cl.
CPC ............ *A24F 47/008* (2013.01); *A24F 15/12* (2013.01); *H05B 1/0244* (2013.01); *H05B 3/40* (2013.01)

(58) Field of Classification Search
CPC ................................ A24F 47/00; A61M 15/06
See application file for complete search history.

(56) References Cited

U.S. PATENT DOCUMENTS 4,945,929 A * 8/1990 Egilmex ............... A24F 47/002 128/200.21
4,945,931 A * 8/1990 Gori ...................... A24F 47/008 131/194
2008/0230052 A1 9/2008 Montaser
(Continued)

FOREIGN PATENT DOCUMENTS

CN 2719043 Y 8/2005
CN 201054977 Y 5/2008
(Continued)

*Primary Examiner* — Cynthia Szewczyk
(74) *Attorney, Agent, or Firm* — Cheng-Ju Chiang

(57) ABSTRACT

An electronic cigarette comprises a main rod body with one end thereof being provided with a suction nozzle and the other end being internally provided with a battery, a one-way valve is provided in the main rod body for providing a gas passage when inhaling gas and shutting off the gas passage The one-way valve comprises a valve seat with two penetrating ends, and a valve core and a valve flap mounted inside the valve seat; the valve seat or the valve core is provided with a gas guide hole; and the valve flap is affixed to an orifice at one end of the gas guide hole and generates elastic deformation corresponding to the operation of inhaling or exhaling gas so as to control the open or closed state of the gas guide hole.

16 Claims, 9 Drawing Sheets

(56) References Cited

U.S. PATENT DOCUMENTS

| | | | | |
|---|---|---|---|---|
| 2010/0126505 A1* | 5/2010 | Rinker | A24F 47/006 | 128/202.21 |
| 2010/0229881 A1* | 9/2010 | Hearn | A24F 47/002 | 131/273 |
| 2012/0138052 A1* | 6/2012 | Hearn | A24F 47/002 | 128/202.21 |
| 2012/0255546 A1* | 10/2012 | Goetz | A61M 11/041 | 128/202.21 |

FOREIGN PATENT DOCUMENTS

| | | |
|---|---|---|
| CN | 101862038 A | 10/2010 |
| CN | 202172846 U | 3/2012 |

* cited by examiner

ELECTRONIC CIGARETTE AND ELECTRONIC CIGARETTE DEVICE THEREOF

CROSS REFERENCE TO RELATED APPLICATIONS

The present application is a 35 U.S.C. §371 National Phase conversion of International (PCT) Patent Application No. PCT/CN2012/082290, filed on Sep. 28, 2012, the disclosure of which is incorporated by reference herein. The PCT International Patent Application was filed and published in Chinese.

FIELD OF THE INVENTION

The present invention relates to electronic cigarette box, especially an electronic cigarette and electronic cigarette device with a one way valve mechanism capable of controlling the direction of airflow.

BACKGROUND OF THE INVENTION

With further understanding of the harm of smoking by people, quit smoking has become the common goal of most smokers. Then, as a substitute for cigarette, electronic cigarette is gradually welcomed by people.

Current electronic cigarette is usually composed of two parts, including an inhalation rod and a battery rod, wherein the inhalation rod usually disposes a suction nozzle and an atomization device operable to make e-liquid into aerosol. The battery rod usually disposes a battery and a control switch therein. The battery is used to supply power, and the control switch is used to control the overall operation of the electronic cigarette. Air path of current electronic cigarette is completely through in both inhaling and blowing conditions. When users blowing to the electronic cigarette, the aerosol and e-liquid in the atomization device always flow to the battery and the control switch driven by action of airflow, leading to resistance of the battery increasing and electrode oxidation, and then cause short circuit, the control switch failure and so on.

SUMMARY OF THE INVENTION

The objective of the present invention is: to provide an electronic cigarette, which has the function of one-way air path control capable of communicating the air path when inhalation and blocking the air path when blowing.

To achieve the aforementioned objective, the present invention discloses an electronic cigarette including a main rod body. One end of the main rod body disposes a suction nozzle, and the other end of the main rod body disposes a battery. The main rod body also disposes a one-way valve used to communicate an air path when inhalation and block the air path when blowing, and is located between the suction nozzle and the battery. The one-way valve comprises a valve seat with both ends throughout, a valve core and a valve flap installed in the valve seat. The valve seat or the valve core disposes a gas guide hole thereon. The valve flap is attached at a port of one end of the gas guide hole and used to control open and close state of the gas guide hole according to corresponding elastic deformation generated by inhalation or blowing operations.

Furthermore, the valve flap comprises a sheet body which is sheet-shaped and, of which the area is bigger than the cross section of the gas guide hole and capable of completely covering the port of one end of the gas guide hole, and a connecting portion locating at one side edge of the sheet body and elastically connected to the valve seat or the valve core.

Furthermore, the valve flap is disposes on an outside of the port of one end of the gas guide hole near the suction nozzle.

Furthermore, one end of the valve seat disposes a valve core-accommodating groove matching with the outer contour of the valve core, the valve core is embedded in the valve core-accommodating groove.

Furthermore, the valve flap is made of soft plastic material.

Furthermore, one end of the main rod body near the suction nozzle further disposes an atomization device electrically connecting with the battery.

Furthermore, the one-way valve is disposed between the suction nozzle and the atomization device.

Furthermore, the one-way valve is disposed between the battery and the atomization device, and one end of the valve seat near the battery disposes vent hole along radial direction communicating with the gas guide hole.

Furthermore, the atomization device disposes a heating wire used to vaporize the e-liquid, the valve seat and the valve core disposes threading hole for the two ends of the heating wire passing through.

Furthermore, the other end of the electronic cigarette away from the suction nozzle disposes a light-emitting device, the light-emitting device comprises a light-emitting unit electrically connecting with the battery and a light cap covering the outer of the light-emitting unit.

Furthermore, at the connection between the light cap and the main rod body disposes an air inlet communicating with the gas guide hole.

Furthermore, on the sidewall of the main rod body corresponding to the battery near one end of the suction nozzle disposes an air inlet communicating with the gas guide hole.

Furthermore, the electronic cigarette further includes an atomization control unit electrically connecting with the battery to control the power-on or power-off for the atomization device, the atomization control unit comprises an atomization control circuit and an atomization control switch which is connected with the atomization control circuit.

Furthermore, the atomization control switch is a capacitive sensor switch or an airflow sensor switch.

A further objective of the present invention is: to provide an electronic cigarette device, in which electronic cigarette is disposed and has the function of one-way air path control.

To achieve the aforementioned objective, the present invention also disclose an electronic cigarette device, including an electronic cigarette box and an electronic cigarettes accommodated in the electronic cigarette box. The electronic cigarette is the electronic cigarette as described above.

The advantages of the embodiments of the present invention is: due to dispose the one-way valve between the suction nozzle and battery of the electronic cigarette, making the electronic cigarette have the function of one-way air path control capable of communicating the air path when inhalation and blocking the air path when blowing.

Embodiments of the present invention will be further described in detail in the following drawings.

DETAILED DESCRIPTION OF THE INVENTION

Referring to FIG. 1 to FIG. 12, the embodiment of the present invention provides an electronic cigarette device including an electronic cigarette 100 capable of one-way air path controlling and an electronic cigarette box 200 operable to accommodate the electronic cigarette 100.

Figure 1:
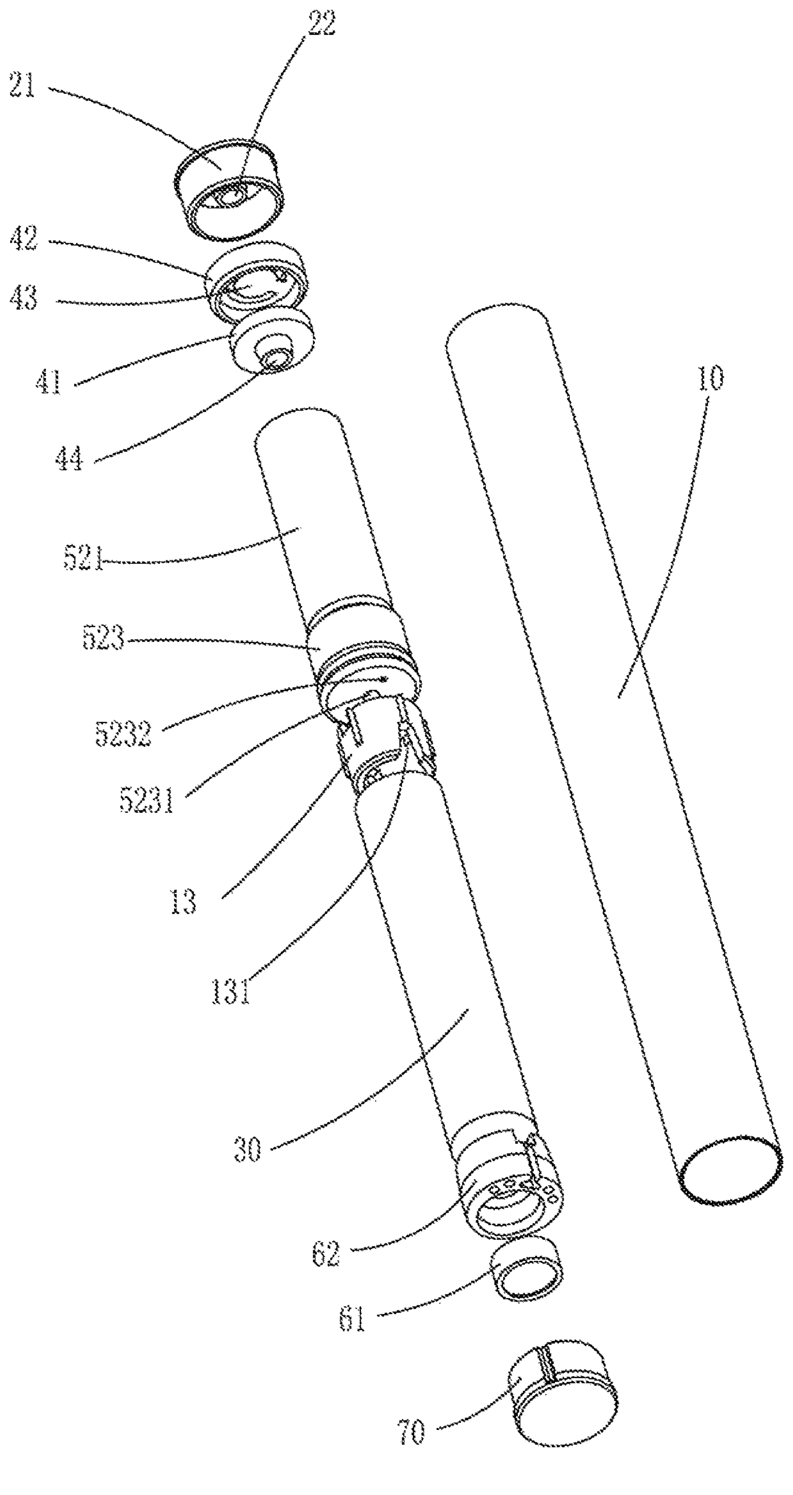
FIG. 1 is an exploded, isometric view of an electronic cigarette according to a first embodiment of the present invention.
Figure 3:
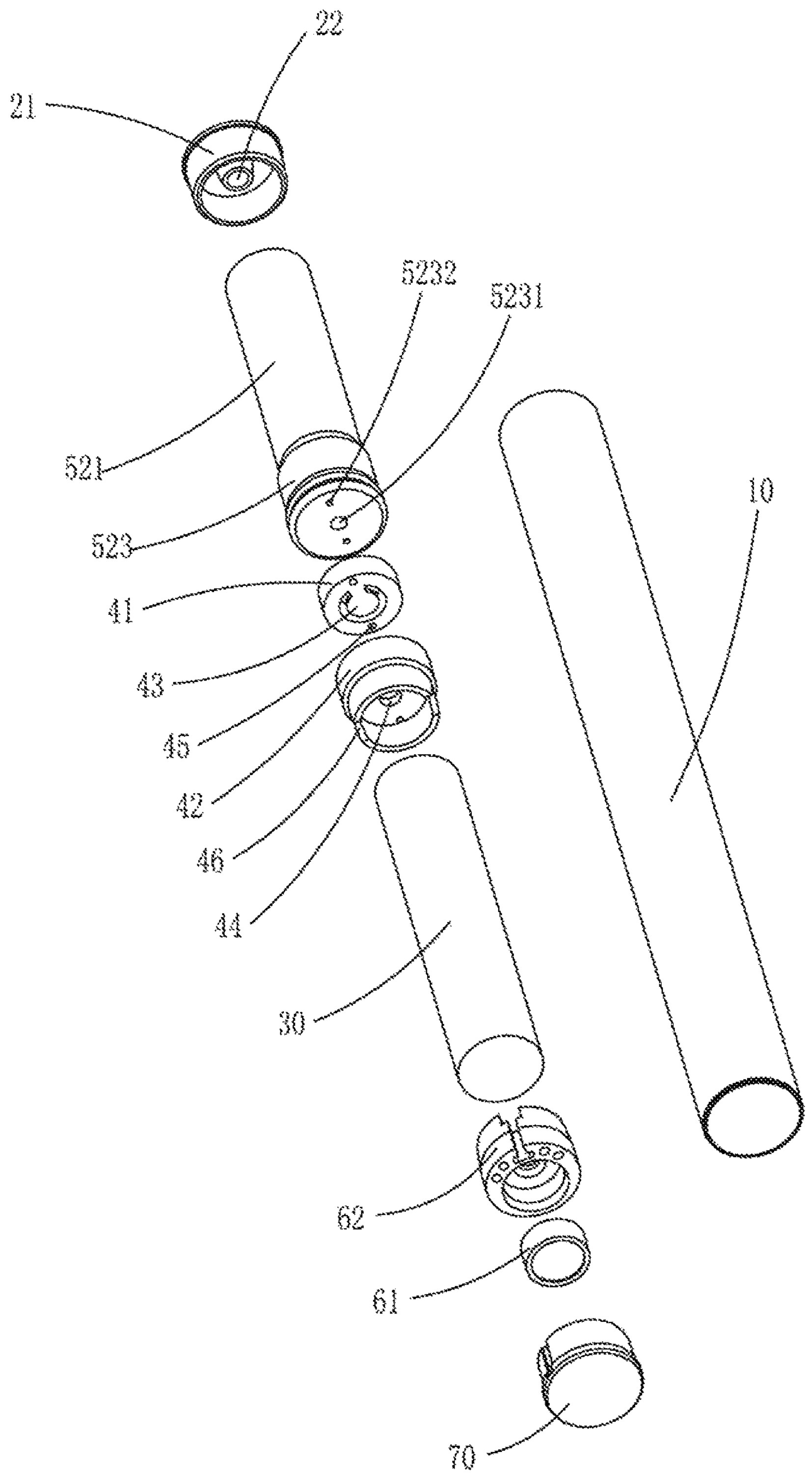
FIG. 3 is an exploded, isometric view of an electronic cigarette according to a second embodiment of the present invention.

Referring to FIG. 1 and FIG. 3, the electronic cigarette 100 includes a main rod body 10. The main rod body 10 is disposed as cylindrical tube structure, and is hollow inside thereof to form an accommodating chamber for all kinds of internal components. It is understood that the main rod body 10 also can be disposed as any other tubular structure arranged with a hollow chamber, but not limited to the cylinder shown in the embodiment. In the embodiment, the main rod body 10 can be made of stainless materials, and also can be made of plastic or other applicable materials.

Figure 2:
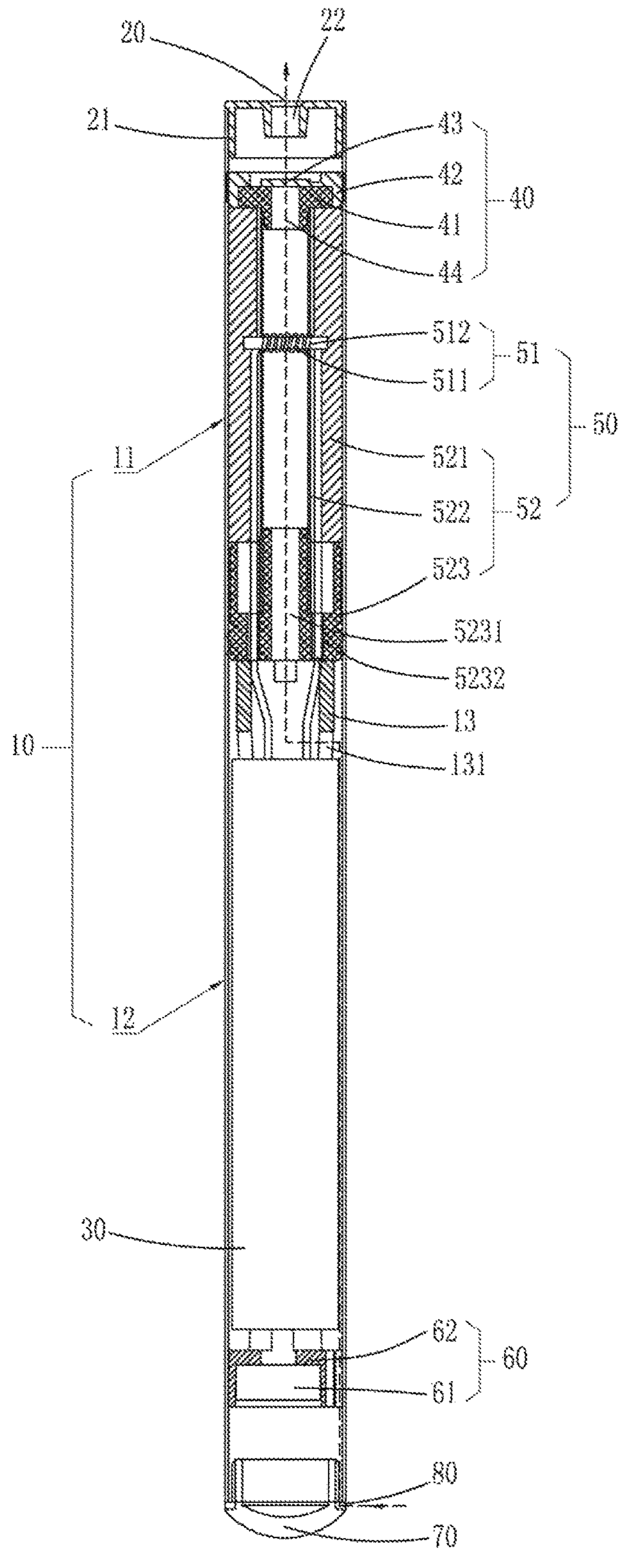
FIG. 2 is a sectional view of an electronic cigarette according to the embodiment of the present invention.
Figure 4:
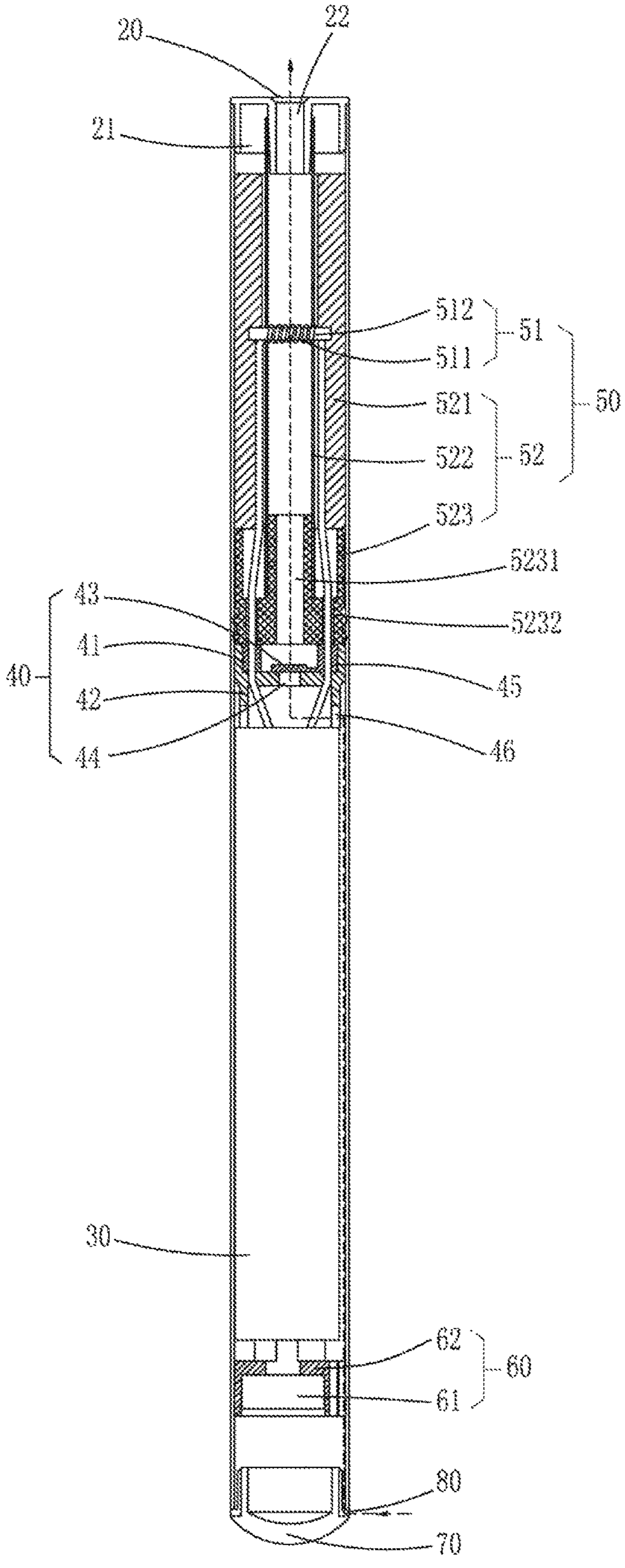
FIG. 4 is a sectional view of an electronic cigarette according to the second embodiment of the present invention.
Figure 5:
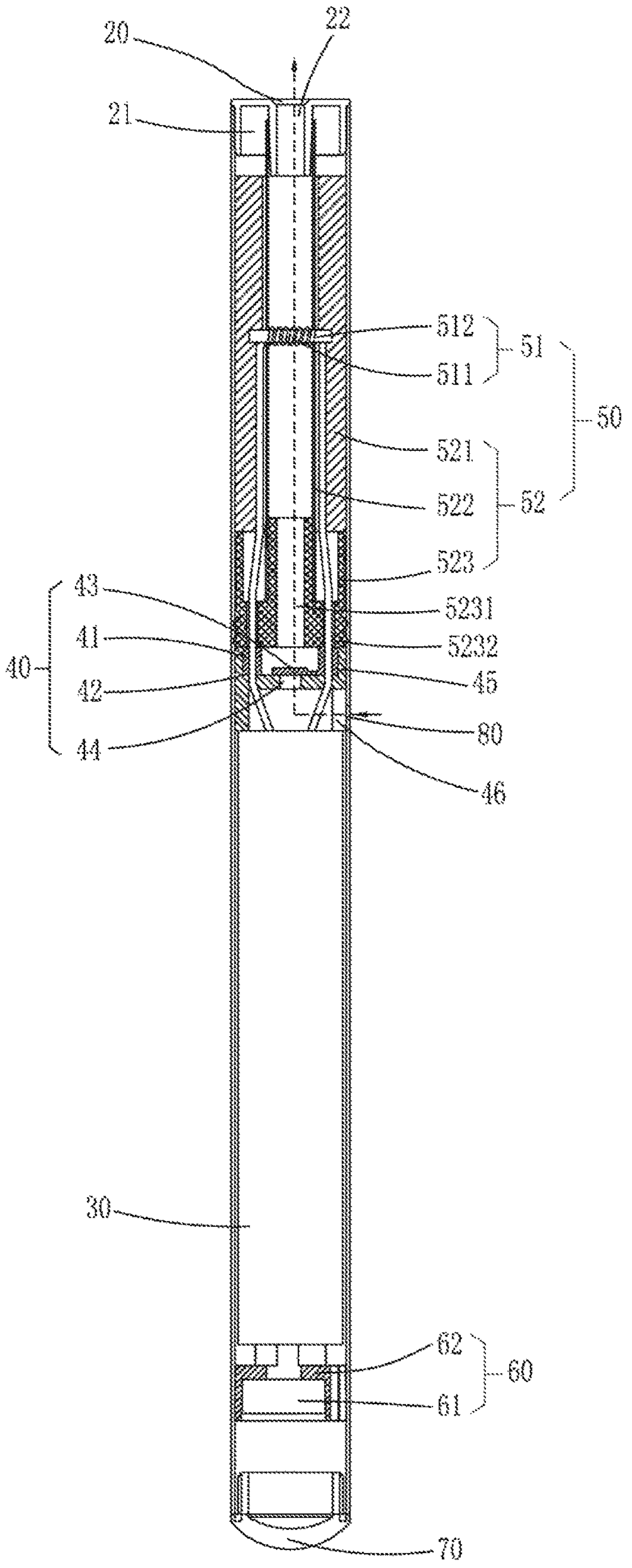
FIG. 5 is a sectional view of an electronic cigarette according to a third embodiment of the present invention.

Referring to FIG. 2, FIG. 4 and FIG. 5, one end of the main rod body 10 disposes a suction nozzle 20, and the other end of the main rod body 10 away from the suction nozzle 20 disposes a battery 30. Therefore, according to the composition of the internal components in the main rod body 10, the main rod body 10 may be divided into two parts as an inhalation rod 11 and a battery rod 12. That is, the main rod body 10 includes the inhalation rod 11 and the battery rod 12 which are mutual butted. In the embodiment, the inhalation rod 11 and the battery rod 12 are designed as undetachable integral structure. As an alternative embodiment, the inhalation rod 11 and the battery rod 12 also can be disposed as a detachably connected, for example, by clamping connection, inserted connection or screwed connection and etc.

The battery 30 is disposed in the battery rod 12 operable to supply power for every function module of the electronic cigarette 100. The suction nozzle 20 is arranged at the other end of the inhalation rod 11 away from the battery 30. In the embodiment, the suction nozzle 20 includes the inhalation cover 21 sheathed on one end of the inhalation rod 11. The inhalation cover 21 axially defines an inhalation hole 22.

Referring to FIG. 1 to FIG. 5, the main rod body 10 disposes an air path throughout the main rod body 10 inside thereof. Between the suction nozzle 20 and the battery 30 disposes a one-way valve 40 operable to control airflow direction of inhalation air path, that is to communicate the air path when inhalation and block the air path when blowing.

Specifically, the one-way valve 40 includes a valve core 41, a valve seat 42 and a valve flap 43. Two ends of the valve seat 42 are throughout. The valve core 41 is disposed in the valve seat 42. The valve seat 42 or the valve core 41 disposes a gas guide hole 44. The valve flap 43 is attached at port of one end of the gas guide hole 44 and operable to control the open and close state of the gas guide hole 44 according to corresponding elastic deformation generated by inhalation or blowing operations.

Figure 6:
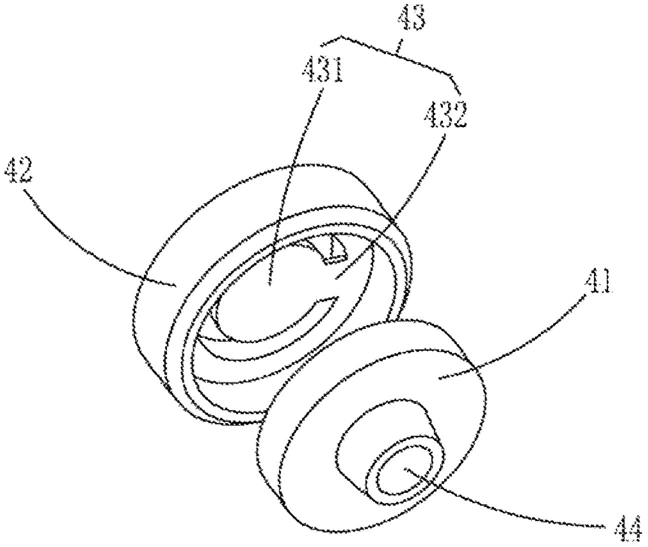
FIG. 6 is an exploded, isometric view of a one-way valve of an electronic cigarette according to a first embodiment of the present invention.
Figure 7:
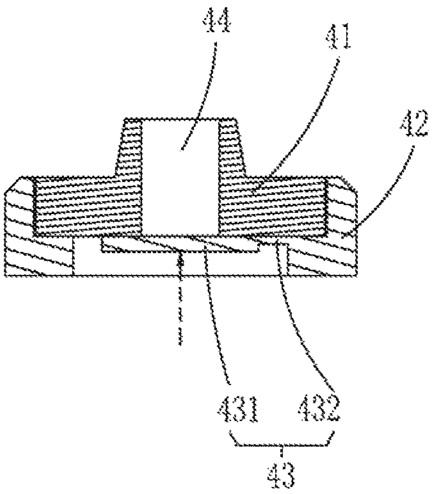
FIG. 7 is a schematic view of Valve flap, the one-way valve of an electronic cigarette according to the first embodiment of the present invention, showing a valve flap being close state.

Referring to FIG. 6 and FIG. 7, the valve flap 43 is disposed at an outside of the port of one end of the gas guide hole 44 near the suction nozzle 20, and can be disposed on the valve core 41 or the valve seat 41 according to facing direction of the one-way valve 40. The valve flap 43 includes a sheet body 431 which is thin-sheet shaped and of which the area is larger than the cross section of the gas guide hole 44 to completely cover the port of one end of the gas guide hole 44, and a connecting portion 432 locating at one side edge of the sheet body 431 and elastically connected to the valve core 41 or the valve seat 42. In the embodiment, the valve flap 43 and the valve core 41 or the valve seat 42 are integrally formed. The sheet body 431 is disposed as circular, and a diameter of the sheet body 431 is bigger than a diameter of the gas guide hole 44 to be capable of completely covering the port of one end of the gas guide hole 44. It is understood that the sheet body 431 of the valve flap 43 also may be disposed as square-shaped, polygonal or other shapes as long as it is guaranteed that the sheet body 431 of the valve flap 43 is capable of completely covering the gas guide hole 44 to close the air path when the valve flap 43 attaching to the gas guide hole 44. As an embodiment, the valve flap 43 and the valve core 41 or the valve seat 42 also may be separately arranged, for example, the connecting portion 432 of the valve flap 43 is firmly fixed between the valve seat 42 and the valve core 41 by clamping connection, inserting connection and other connection methods.

In the embodiment, the valve flap 43 is made of soft plastic materials such as rubber, silicone rubber, thermoplastic polyurethane elastic plastic and etc, making the valve flap 43 capable of producing certain elastic deformation under airflow pressure to achieve communicating and close of the air path thereof.

Figure 8:
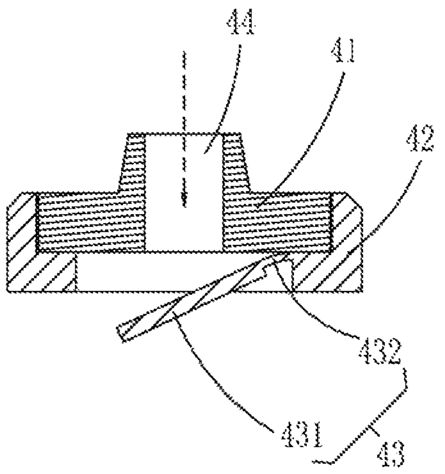
FIG. 8 is a schematic view of the one-way valve of an electronic cigarette according to the first embodiment of the present invention, showing a valve flap being open state.

In a first embodiment as shown in FIG. 6 to FIG. 8, the valve flap 43 is disposed on the valve seat 42, and the gas guide hole 44 is disposed on the valve core 41. Specifically, one side of the valve seat 42 near the valve core 41 disposes a valve core-accommodating groove matching with the outer contour of the valve core 41 to sheath on the valve core 41. The valve core 41 is embedded in the valve core-accommodating groove. The valve flap 43 is attached on the outer surface of the valve core 41 and covers the gas guide hole 44. Referring to FIG. 7 and FIG. 8, the direction of the arrow as shown in the figures is airflow direction. When airflow flows from the valve seat 42 toward the valve core 41, the valve flap 43 is firmly attached on the outside of the port of one end of the gas guide hole 44 under the airflow pressure, then the gas guide hole 44 is closed and the air path is blocked; When airflow flows from the valve core 41 toward the valve seat 42, the valve flap 43 generates elastic deformation under the airflow pressure, and the sheet body 431 away from the inner wall of the valve seat 42 separates from the valve core 41 and gradually moves away from the gas guide hole 44, then finally achieves the communication of the air path.

Figure 9:
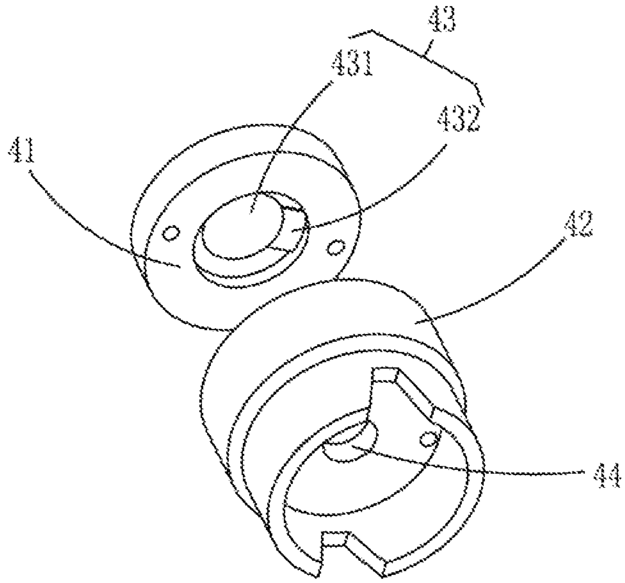
FIG. 9 is an exploded, isometric view of a one-way valve of an electronic cigarette according to a second embodiment of the present invention.
Figure 10:
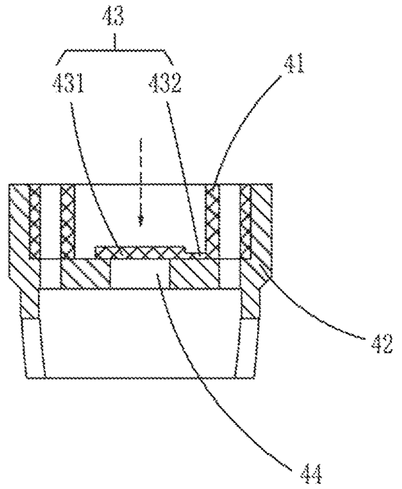
FIG. 10 is a schematic view of the one-way valve of an electronic cigarette according to the first embodiment of the present invention, showing a valve flap being close state.
Figure 11:
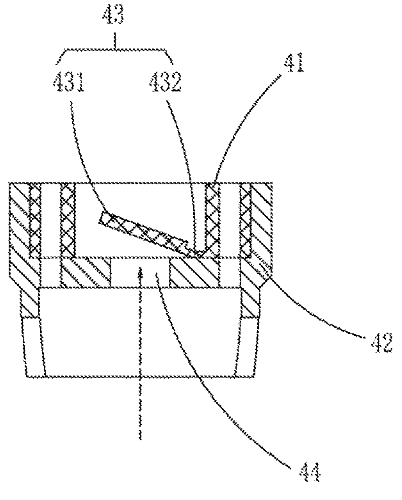
FIG. 11 is a schematic view of the one-way valve of an electronic cigarette according to the first embodiment of the present invention, showing a valve flap being open state.

In a second embodiment as shown in FIG. 9 to FIG. 11, in the embodiment, the valve flap 43 is disposed on the valve core 41, and the gas guide hole 44 is disposed in the valve seat 42. One side of the valve seat 42 near the valve core 41 disposes a valve core-accommodating groove matching with the outer contour of the valve core 41 to sheath on the valve core 41. The valve core 41 is embedded in the valve core-accommodating groove. The valve flap 43 locates at one side of the valve core 41 near to the valve seat 42 and is attached on the inner surface of the valve core- accommodating groove and completely covers the port of one side of the gas guide hole 44. Referring to FIG. 10 and FIG. 11, the direction of the arrow as shown in the figures is airflow direction. When airflow flows from the valve core 41 toward the valve seat 42, the valve flap 43 is firmly attached on the outside of the port of one end of the gas guide hole 44 under the airflow pressure, then the gas guide hole 44 is closed and the air path is blocked; When airflow flows from the valve seat 42 toward the valve core 41, the valve flap 43 generates elastic deformation under the airflow pressure, and the sheet body 431 separates from the valve seat 42 and gradually moves away from the gas guide hole 44, then finally achieves the communication of the air path.

Referring to FIG. 1 to FIG. 5, in the main rod body 10 also disposes an atomization device 50 operable to vaporize e-liquid to become aerosol. In the embodiment, the atomization device 50 is disposed at the inhalation rod 11 of the main rod body 10, and includes an atomizer 51 and an atomization cup 52 used to accommodate the atomizer 51.

The atomizer 51 is used to vaporize e-liquid to become aerosol, and includes a heating wire 511 and a liquid-guiding member such as a fiber piece 512. The heating wire 511 winds on the fiber piece 512, and is accommodated and fixed in the atomization cup 52 by using the fiber piece 512. In the embodiment, the fiber piece 512 is made of fiberglass or other high temperature resistant fiber materials, and used to absorb e-liquid for the heating wire 511 to heat and vaporize e-liquid. The shape of the fiber piece 512 is disposed as cylindrical.

The atomization cup 52 includes a liquid-storage member 521, a support tube 522 and an atomization seat 523. Both the liquid-storage member 521 and the support tube 522 are substantially cylindrical and coaxially arranged.

The liquid-storage member 521 is a hollow cylindrical structure, and is capable of absorbing and storing liquid like a sponge for absorbing and storing e-liquid to facilitate the atomizer 51 to vaporize the e-liquid subsequently. In the embodiment, the liquid-storage member 521 may be made of fiberglass, absorbent cotton and other materials capable of absorbing and storing liquid. The liquid-storage member 521 is sheathed in the main rod body 10 and tensioningly assembled with the inner wall of the main rod body 10.

The support tube 522 also is a hollow cylindrical structure, and is made of fiberglass material. The support tube 522 is sheathed in the liquid-storage member 521 to fix the liquid-storage member 521 in the main rod body 10, and is operable to communicate the air path and play a supporting role for the liquid-storage member 521. The upper sidewall of the support tube 522 disposes a bayonet radially through the sidewall. The bayonet is used to clamp and fix the fiberglass piece 512 of the atomizer 51. Two ends of the fiberglass piece 512 extend out of the support tube 522 from the bayonet and abut with the inner wall of the liquid-storage member 521 to absorb e-liquid in the liquid-storage member 521 for the heating wire 511 to heat and vaporize.

The atomization seat 523 is used to support and fix the atomizer 51 and the atomization cup 52. The atomization seat 523 and the inhalation cover 21 are respectively sealed in two ends of the atomization cup 52 to form a cup body of the atomization cup 52. The atomization seat 523 may be made of plastic material, and the shape and dimension of the atomization seat 523 matches with the inner wall of the main rod body 10 to be tensioningly fixed in the main rod body 10 by the outer sidewall. In the embodiment, the atomization seat 523 is cylindrical, and disposes a first gas guide hole 5231 throughout the atomization seat 523 along axial direction and a plurality of first threading hole 5232 for the heating wire 511 through.

Referring also to FIG. 1 to FIG. 5, one end of the main rod body 10 away from the suction nozzle 20 disposes an atomization control unit 60 which is electrically connected with the battery 30 and used to control power-on or power-off of the atomization device 50. The atomization control unit 60 includes an atomization control circuit and an atomization control switch 61 which is electrically connected with the atomization control circuit. The atomization control switch 61 is fixed in the main rod body 10 by a switch fixing seat 62.

In the embodiment, the atomization control switch 61 is a sensor switch, specifically, the sensor switch is a capacitive sensor switch. When users using the electronic cigarette 100 for smoking, the capacitive sensor switch sensors the capacitance change after inhalation of airflow and then controls the atomization control circuit to switch on the power supply, making the electronic cigarette 100 be in working state. As an alternative embodiment, the sensor switch may also be disposed as an airflow sensor switch, that is when users inhaling by the suction nozzle 20, the chamber of the electronic cigarette 100 generates negative pressure to make the airflow sensor switch generating pulse signals to control the atomization control circuit to switch on the power supply.

Because manufacturing of the sensor switch is of precision, and the sensor switch generally disposes a special controller therein, the atomization control circuit of the present embodiment may be directly integrated on the controller in the sensor switch. As an alternative embodiment, the atomization control circuit also may be integrated on an atomization control circuit board which is independently disposed at the outer of the sensor switch and connected with the sensor switch and the battery 30 respectively. As an alternative embodiment, the atomization control switch 61 also may be disposed as a traditional key switch.

Referring to FIG. 1 to FIG. 5, the other end of the main rod body 10 away from the suction nozzle 10 also disposes a light-emitting device. The light-emitting device is used as a work indicating light of the electronic cigarette 100, and includes a light-emitting unit electrically connected with the battery 30 and a light cap 70 which is sheathed on the outer of the light-emitting unit.

Referring to FIG. 1 and FIG. 2, FIG. 1 and FIG. 2 shows a first embodiment of the present invention. In the embodiment, the one-way valve 40 is disposed between the suction nozzle 20 and the atomization device 50. At the connection between the light cap 70 and the main rod body 10 disposes an air inlet 80 communicating with the gas guide hole 44 to form the inhalation air path in the main rod body 10 throughout the main rod body 10. Referring to FIG. 2, the direction indicated by arrow shown FIG. 2 is airflow direction of the inhalation air path of the embodiment.

Specifically, the valve seat 42 is sheathed at the outer of the valve core 41 and tensioningly fixed in the main rod body 10 by using the outer wall. Meanwhile, the valve core 41 is abutted between the valve seat 42 and the atomization device 50. The middle of the valve core 41 extends along axial direction to form a support column extending into the support tube 522. The gas guide hole 44 communicates with the first gas guide hole 5231 of the atomization seat 523 by the support tube 522. The atomization seat 523 abuts with the battery 30 by a bracket 13. One end of the bracket 13 near the battery 30 disposes a second gas guide hole 131 axially throughout the sidewall of the bracket 13.

When users using the electronic cigarette 100 of the present embodiment smoking, users align with the inhalation hole 22 of the suction nozzle 20 to inhale, external air enters into the main rod body 10 through the air inlet 80 at the connection between the light cap 70 and the main rod body 10. Air enters into the atomization device 50 along the sidewall of the battery rod 12 through the second gas guide hole 131 on the sidewall of the bracket 13., when air flows through the support tube 522 of the atomization device 50, airflow drives the aerosol vaporized by the atomizer 51 to flow toward the suction nozzle 20. When air flows through the gas guide hole 44, the valve flap 43 generates elastic deformation under airflow pressure and separates from the gas guide hole 44, then the gas guide hole 44 is through, the aerosol flows out from the inhalation hole 22 through the gas guide hole 44 along with the airflow and finally inhaled by human body. When blowing, airflow flows reversely, the valve flap 43 is firmly attached with the end surface of the corresponding vent port of the gas guide hole 44 under the airflow pressure by blowing, then the gas guide hole 44 is sealed, the blowing airflow is blocked and unable to enter into the atomization device 50. The aerosol and the e-liquid in the atomization device 50 never flows to the battery 30 and the atomization control switch 61 without airflow driven, therefore avoid the damage of the battery 30 and the atomization control switch 61 caused by the aerosol and the e-liquid, ensuring the working life of the electronic cigarette 100.

Referring to FIG. 3 and FIG. 4, FIG. 3 and FIG. 4 shows a second embodiment of the present invention. In the embodiment, the one-way valve 40 is disposed between the battery 30 and the atomization device 50. Also, at the connection between the light cap 70 and the main rod body 10 disposes the air inlet 80 communicating with the gas guide hole 44 to form an inhalation air path throughout the main rod body 10. Referring to FIG. 4, the direction indicated by arrow shown FIG. 4 is airflow direction of the inhalation air path of the embodiment.

Specifically, in the embodiment, the valve seat 42 is sheathed at the external of the valve core 41 and tensioningly fixed in the main rod body 10 by using the outer wall thereof. The valve core 41 is firmly abutted between the valve seat 42 and the atomization device 50 by the valve seat 42. The valve seat 42 and the valve core 41 correspondingly disposes a second threading hole 45 for the two ends of the heating wire 511 passing through, and one end of the valve seat 42 near the battery 30 axially disposes a third gas guide hole 46 communicating with the gas guide hole 44.

When users using the electronic cigarette 100 of the present embodiment smoking, users align the inhalation hole 22 to inhale, external air enters into the main rod body 10 through the air inlet 80 at the connection between the light cap 70 and the main rod body 10. Air enters into the gas guide hole 44 along the sidewall of the battery rod 12 through the third gas guide hole 46 on the sidewall of the valve seat 42, the valve flap 43 generates elastic deformation under airflow pressure and separates from the gas guide hole 44, then the gas guide hole 44 is through, the airflow enters in to the support tube 522 through the first gas guide hole 5231 which is axially through on the atomization seat 523. When flowing through the atomizer 51, airflow drives the aerosol vaporized by the atomizer 51 to flow out from the inhalation hole 22 and finally inhaled by human body. When blowing, the airflow flows reversely and when reaching the one-way valve 40, the valve flap 43 is firmly attached with the end surface of the corresponding vent port of the gas guide hole 44 under the airflow pressure, then seals the air path of the blowing airflow. At this time, because the blowing airflow is blocked by the one-way valve 40, aerosol and e-liquid in the atomization device 50 is blocked at one side of the one-way valve 40 near the atomization device 50, then avoid aerosol and e-liquid entering into the battery rod 12 to affect the working life of the battery 30 and the atomization control switch 61 in the battery rod 12.

Referring to FIG. 5, FIG. 5 shows a third embodiment of the present invention. In the embodiment, the one-way valve 40 is disposed at the same position as the aforementioned second embodiment, and is also located between the battery 30 and the atomization device 50. The difference is that the air inlet 80 is disposed on the sidewall of one end of the main rod body 10 corresponding to the battery 30 near the inhalation rod 11, therefore blowing airflow directly enters into the inhalation rod 11 without passing the battery rod 12. When the air inlet 80 is disposed on the sidewall of the main rod body 10, the third gas guide hole 46 on the valve seat 42 may be only disposed on the sidewall of the end corresponding to the air inlet 80. Certainly, the air inlet 80 specified in the present embodiment also may be disposed at any proper position on the sidewall of the main rod body 10; or may be disposed at the connection between the main rod body 10 and the light cap 70 simultaneously, as long as it is assured that the inhalation airflow is capable of entering into the atomization device 50 to drive the vaporized aerosol flowing out from the suction nozzle 20 for human body inhalation.

When users using the electronic cigarette 100 of the present embodiment smoking, users align the inhalation hole 22 to inhale, external air enters into the gas guide hole 44 through the air inlet 80 disposed on the sidewall of the main rod body 10 and the third gas guide hole 46 disposed on the sidewall of the valve seat 42, the valve flap 43 generates elastic deformation under airflow pressure and separates from the gas guide hole 44, then the gas guide hole 44 is through, the airflow enters in to the support tube 522 through the gas guide hole 44 and the first gas guide hole 5231 of the atomization seat 523, and drives the aerosol vaporized by the atomizer 51 to flow out from the inhalation hole 22 when flowing through the atomizer 51, then make human body inhale the vaporized aerosol. Similarly to the second embodiment, the valve flap 43 seals the gas guide hole 44 under the blowing airflow pressure, then avoid the aerosol and the e-liquid entering into the battery rod 12 along with the blowing airflow, therefore effectively guarantees the working life of the battery 30 and the atomization control switch 61.

It is understood that the electronic cigarette 100 described in the embodiment of the present invention is not only limited to the three embodiments shown in FIG. 1 and FIG.

5. The technology characteristics of these embodiments can be combined with each other to form new embodiments.

Figure 12:
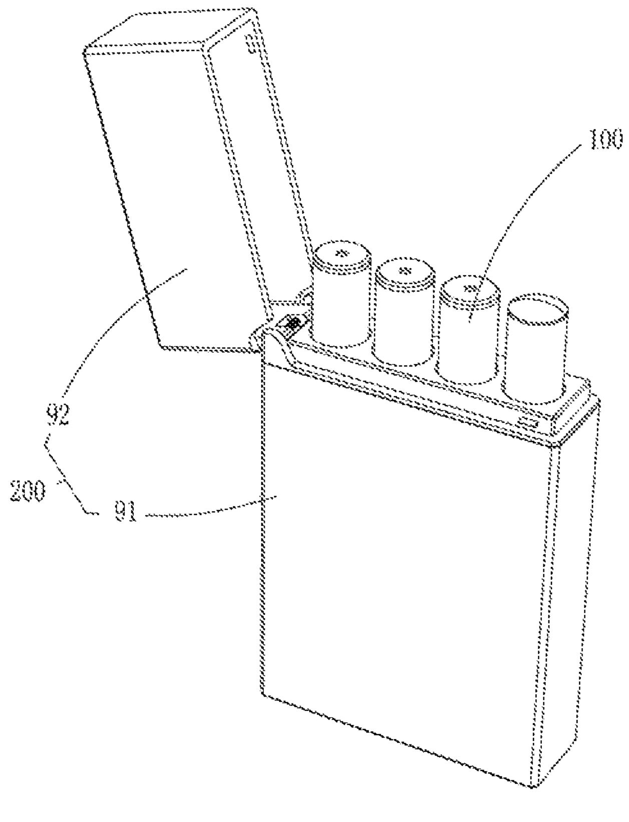
FIG. 12 is an isometric view of an electronic cigarette device according to an embodiment of the present invention.

Referring to FIG. 12, the electronic cigarette 100 is generally placed in the electronic cigarette box 200. The electronic cigarette box 200 includes a bottom box 91 operable to accommodate the electronic cigarette 100 and a box cover 92 covering the bottom box 91. The bottom box 91 is a square shell structure, and certainly, the shape is not limited to square, and also may be circular, oval, polygonal and etc as long as it is ensured that the box cover 92 matches with the bottom box 91 when arranging the box cover 92.

Embodiments of the present invention is shown and described in the above-mentioned. Various improvement and modifications can be made to the embodiments by those skilled in the art without departing from the true spirit and scope of the disclosure. The scope of the present invention is defined by the appended claims and equivalents thereof.

What is claimed is:

1. An electronic cigarette, comprising:

a main rod body, one end of the main rod body disposing a suction nozzle, and the other end of the main rod body disposing a battery; and a one-way valve disposed in the main rod body and configured to communicate an air path when inhalation and block the air path when blowing, the one-way valve being located between the suction nozzle and the battery;

wherein the one-way valve comprises a valve seat with both ends throughout, a valve core and a valve flap installed in the valve seat, the valve seat or the valve core defines a gas guide hole therein; the valve flap is attached at a port of one end of the gas guide hole and used to control open and close state of the gas guide hole according to corresponding elastic deformation generated by inhalation or blowing operations;

the valve flap is disposed on the valve core or the valve seat, and comprises a sheet body and a connecting portion; the valve flap is thin-sheet shaped with an area larger than the gas guide hole to completely cover the port of one end of the gas guide hole; the connecting portion is located at one side edge of the sheet body;

the valve flap is connected to the valve seat, and the gas guide hole is defined in the valve core, one side of the valve seat defines a valve core-accommodating groove matching with an outer contour of the valve core, the valve core is embedded in the valve core-accommodating groove, the valve flap is attached on an outer surface of the valve core and covers the gas guide hole, whereby airflow flows from the valve seat toward the valve core, the valve flap is firmly attached on an outside of the port of one end of the gas guide hole under the airflow pressure, then the gas guide hole is closed and the air path is blocked; while airflow flows from the valve core toward the valve seat, the valve flap generates elastic deformation under the airflow pressure, and the sheet body moves away from the gas guide hole, then finally achieves the communication of the air path; or the valve flap is connected to the valve core, and the gas guide hole is defined in the valve seat, one side of the valve seat defines a valve core-accommodating groove matching with the outer contour of the valve core, the valve core is embedded in the valve core-accommodating groove, the valve flap locates at one side of the valve core near to the valve seat and is attached on an inner surface of the valve core-accommodating groove and completely covers the port of one side of the gas guide hole, whereby airflow flows from the valve core toward the valve seat, the valve flap is firmly attached on an outside of the port of one end of the gas guide hole under the airflow pressure, then the gas guide hole is closed and the air path is blocked, while airflow flows from the valve seat toward the valve core, the valve flap generates elastic deformation under the airflow pressure, and the sheet body separates from the valve seat and moves away from the gas guide hole, then finally achieves the communication of the air path.

2. According to the electronic cigarette in claim 1, wherein the valve flap is integrally formed with the valve core or the valve seat; or the valve flap is separately arranged, and the connecting portion of the valve flap is firmly fixed between the valve seat and the valve core by a connection method.

3. According to the electronic cigarette in claim 1, wherein the valve flap is made of soft plastic material.

4. According to the electronic cigarette in claim 1, wherein one end of the main rod body near the suction nozzle further disposes an atomization device electrically connecting with the battery.

5. According to the electronic cigarette in claim 4, wherein the one-way valve is disposed between the suction nozzle and the atomization device.

6. According to the electronic cigarette in claim 4, wherein the one-way valve is disposed between the battery and the atomization device, and one end of the valve seat near the battery disposes vent hole along radial direction communicating with the gas guide hole.

7. According to the electronic cigarette in claim 6, wherein the atomization device disposes a heating wire used to vaporize the e-liquid, the valve seat and the valve core disposes threading hole for the two ends of the heating wire passing through.

8. According to the electronic cigarette in claim 4, wherein the electronic cigarette further includes an atomization control unit electrically connecting with the battery to control the power-on or power-off for the atomization device, the atomization control unit comprises an atomization control circuit and an atomization control switch which is connected with the atomization control circuit.

9. According to the electronic cigarette in claim 8, wherein the atomization control switch is a capacitive sensor switch or an airflow sensor switch.

10. According to the electronic cigarette in claim 1, wherein the other end of the electronic cigarette away from the suction nozzle disposes a light-emitting device, the light-emitting device comprises a light-emitting unit electrically connecting with the battery and a light cap covering the outer of the light-emitting unit.

11. According to the electronic cigarette in claim 10, wherein at the connection between the light cap and the main rod body disposes an air inlet communicating with the gas guide hole.

12. According to the electronic cigarette in claim 1, wherein on the sidewall of the main rod body corresponding to the battery near one end of the suction nozzle disposes an air inlet communicating with the gas guide hole.

13. An electronic cigarette device, comprising:

an electronic cigarette box; and an electronic cigarette accommodated in the electronic cigarette box, the electronic cigarette comprising:

a main rod body, one end of the main rod body disposing a suction nozzle, and the other end of the main rod body disposing a battery; and a one-way valve disposed in the main rod body and used to communicate an air path when inhalation and block the air path when blowing, the one-way valve being located between the suction nozzle and the battery;

wherein the one-way valve comprises a valve seat with both ends throughout, a valve core and a valve flap installed in the valve seat, the valve seat or the valve core defines a gas guide hole therein; the valve flap is attached at a port of one end of the gas guide hole and used to control open and close state of the gas guide hole according to corresponding elastic deformation generated by inhalation or blowing operations;

the valve flap is disposed on the valve core or the valve seat, and comprises a sheet body and a connecting portion; the valve flap is thin-sheet shaped with an area larger than the gas guide hole to completely cover the port of one end of the gas guide hole; the connecting portion is located at one side edge of the sheet body;

the valve flap is connected to the valve seat, and the gas guide hole is defined in the valve core, one side of the valve seat defines a valve core-accommodating groove matching with an outer contour of the valve core, the valve core is embedded in the valve core-accommodating groove, the valve flap is attached on an outer surface of the valve core and covers the gas guide hole, whereby airflow flows from the valve seat toward the valve core, the valve flap is firmly attached on an outside of the port of one end of the gas guide hole under the airflow pressure, then the gas guide hole is closed and the air path is blocked; while airflow flows from the valve core toward the valve seat, the valve flap generates elastic deformation under the airflow pressure, and the sheet body moves away from the gas guide hole, then finally achieves the communication of the air path; or the valve flap is connected to the valve core, and the gas guide hole is defined in the valve seat, one side of the valve seat defines a valve core-accommodating groove matching with the outer contour of the valve core, the valve core is embedded in the valve core-accommodating groove, the valve flap locates at one side of the valve core near to the valve seat and is attached on an inner surface of the valve core-accommodating groove and completely covers the port of one side of the gas guide hole, whereby airflow flows from the valve core toward the valve seat, the valve flap is firmly attached on an outside of the port of one end of the gas guide hole under the airflow pressure, then the gas guide hole is closed and the air path is blocked, while airflow flows from the valve seat toward the valve core, the valve flap generates elastic deformation under the airflow pressure, and the sheet body separates from the valve seat and moves away from the gas guide hole, then finally achieves the communication of the air path.

14. According to the electronic cigarette device in claim 13, wherein the valve flap is integrally formed with the valve core or the valve seat, or the valve flap is separately arranged, and the connecting portion of the valve flap is firmly fixed between the valve seat and the valve core by a connection method.

15. According to the electronic cigarette device in claim 13, wherein the valve flap is made of soft plastic material.

16. According to the electronic cigarette device in claim 13, wherein one end of the main rod body near the suction nozzle further disposes an atomization device electrically connecting with the battery.

* * * * *